US00PP34309P2

(12) United States Plant Patent
Bergman

(10) Patent No.: US PP34,309 P2
(45) Date of Patent: Jun. 7, 2022

(54) ***CHRYSANTHEMUM* PLANT NAMED 'CIDZ0109'**

(50) Latin Name: ***Chrysanthemum* x *morifolium***
Varietal Denomination: CIDZ0109

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/361,491

(22) Filed: Jun. 29, 2021

(51) Int. Cl.
*A01H 5/02* (2018.01)
*A01H 6/14* (2018.01)

(52) U.S. Cl.
USPC ..... Plt./286

(58) Field of Classification Search
USPC ..... Plt./286
CPC ... A01H 5/02; A01H 5/00; A01H 6/14; A01H 6/1424; A01H 6/385; A01H 5/0255; A01H 6/36
See application file for complete search history.

(56) References Cited

PUBLICATIONS

Upov Pluto Plant Variety Database Sep. 4, 2021, retrieved on Sep. 7, 2021, retrieved from the Internet at https://www3.wipo.int/pluto/user/en/index.jsp, one page. (Year: 2021).*

* cited by examiner

*Primary Examiner* — June Hwu
(74) *Attorney, Agent, or Firm* — Dale Skalla

(57) ABSTRACT

A new *Chrysanthemum* plant named 'CIDZ0109' having medium sized red and yellow striped bicolored daisy-type inflorescences, strong and uniform plant habit, and a flowering response time of 7.5 weeks.

1 Drawing Sheet

Figure 1:
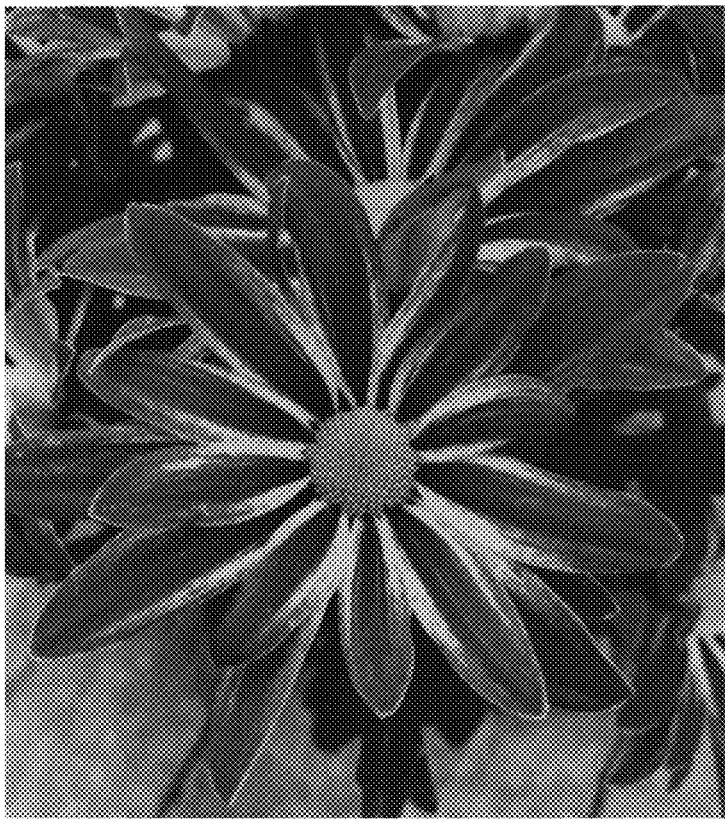

Latin name of the genus and species of the plant claimed: *Chrysanthemum* x *morifolium.*

Varietal denomination: 'CIDZ0109'.

BACKGROUND OF THE NEW PLANT

The present invention comprises a new *Chrysanthemum*, botanically known as *Chrysanthemum* x *morifolium*, and hereinafter referred to by the variety name 'CIDZ0109'.

'CIDZ0109' is a product of a planned breeding program. The new cultivar has medium sized red and yellow striped bicolored daisy-type inflorescences, strong and uniform plant habit, and a flowering response time of 7.5 weeks.

'CIDZ0109' originated from a hybridization made in March 2018 in a greenhouse in Gilroy, Calif. The female parent was the unpatented, proprietary breeding line designated as 'F0448', with red and yellow striped bicolored daisy-type inflorescences, a smaller flower size, more compact plant, and slower flowering response when compared to 'CIDZ0109'.

The male parent of 'CIDZ0109' was the unpatented, proprietary breeding line designated as 'B7948', having red daisy-type inflorescences, a more vigorous growth habit, and faster flowering response than 'CIDZ0109'.

The seed was sown in August 2018 and the resulting plants were grown out doors in a field covered by saran in Fort Myers, Fla. 'CIDZ0109' was selected as one flowering plant within the progeny of the stated cross in December 2018.

The first act of asexual reproduction of 'CIDZ0109' was accomplished when vegetative cuttings were propagated from the initial selection in March 2019, in Fort Myers, Fla.

BRIEF SUMMARY OF INVENTION

Horticultural examination of plants grown from cuttings of the plant initiated in March, 2019 and continuing thereafter, has demonstrated that the combination of characteristics as herein disclosed for 'CIDZ0109' are firmly fixed and are retained through successive generations of asexual reproduction.

'CIDZ0109' has not been observed under all possible environmental conditions. The phenotype may vary significantly with variations in environment such as temperature, light intensity and day length.

A Plant Breeder's Right was applied for in Canada on Aug. 4, 2021, No. 21-10678. 'CIDZ0109' has not been made publicly available prior to the effective filing date of this application, notwithstanding any disclosure that may have been made less than one year prior to the effective filing date of this application by the inventor or another who obtained 'CIDZ0109' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0109' with colors being as true as possible with an illustration of this type. The photographic drawings show in FIG. 1 a close-up view of an inflorescence, and in FIG. 2 a flowering plant of the new variety.

DETAILED BOTANICAL DESCRIPTION

The plant descriptions and measurements were taken indoors in Hollister, Calif. in May 2021 on about 9 week old plants. Unrooted cuttings had been planted, 4 plants per pot, in 6 inch pots on Mar. 3, 2021. The plants were pinched and moved to short days on Mar. 24, 2021 to induce flowering.

Figure 2:
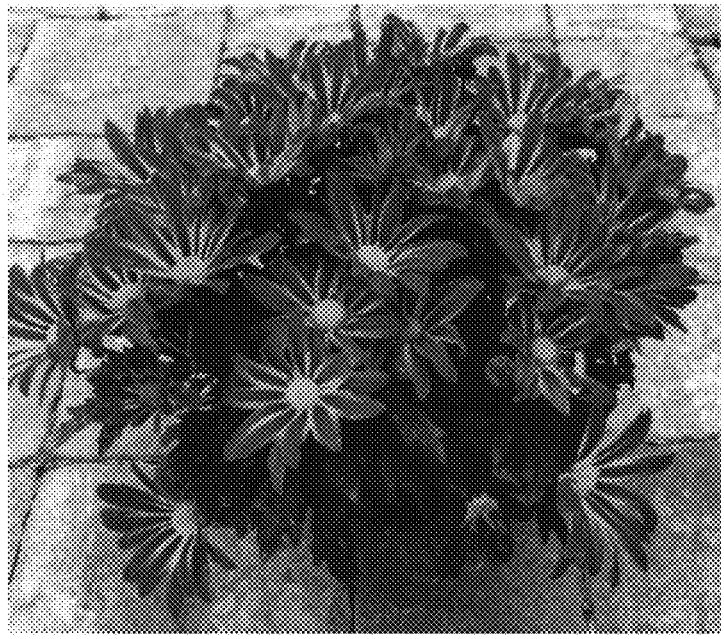

The aforementioned photographs: FIGS. 1 and 2 were taken of the same plants used for the descriptions and measurements in Hollister, Calif. in May of 2021.

Color references are made to The Royal Horticultural Society Colour Chart (R.H.S.) 2001.

TABLE 1

DIFFERENCES BETWEEN THE NEW VARIETY 'CIDZ0109' AND A MOST SIMILAR VARIETY:

| | 'CIDZ0109' | 'Yosun City', U.S. Plant Pat. No. 17,460 |
|---|---|---|
| Plant size and habit: | Shorter | Taller |
| Flowering response: | Faster | Slower |
| Flower size: | Smaller | Larger |

Plant:

*Form, growth and habit.*—Herbaceous pot-type, stems upright to moderately angled, freely branching, strong and compact growth habit.

*Plant height.*—17.0 cm.

*Plant height (inflorescence included).*—21.0 cm.

*Plant width.*—30.0-32.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—RHS 137A.

*Lower surface.*—RHS 138A.

*Mature, leaf color, upper surface.*—RHS 139A.

*Lower surface.*—RHS 137B.

*Length.*—6.7-8.0 cm.

*Width.*—4.5-6.7 cm.

*Shape.*—Ovate.

*Base shape.*—Attenuate.

*Apex shape.*—Mucronate.

*Margin.*—Palmately lobed; irregularly incised, somewhat serrate.

*Number of margin indentations.*—Few.

*Texture, upper surface.*—Puberlulent.

*Lower surface.*—Puberlulent.

*Color of veins, upper surface.*—RHS 138B.

*Color of veins, lower surface.*—RHS 137B.

*Pattern of veining.*—Palmate.

*Stipule.*—Irregularly present.

*Stipule length.*—0.1-1.2 cm.

*Stipule color.*—RHS 137A.

*Petiole color.*—RHS 139A.

*Length.*—1.5-2.7 cm.

*Diameter.*—0.4-0.6 cm.

*Texture.*—Puberlulent.

Stem:

*Quantity of main branches per plant.*—4-5.

*Color of stem.*—RHS 138B.

*Length of stem.*—8.5-11.0 cm.

*Diameter.*—0.4-0.6 cm.

*Length of internodes.*—0.6-2.6 cm.

*Texture.*—Puberlulent.

*Color of peduncle.*—RHS 138B.

*Length of peduncle.*—3.1-6.4 cm.

*Peduncle diameter.*—0.25-0.35 cm.

*Texture.*—Puberlulent.

Inflorescence:

*Type.*—Compositae type, single-type inflorescences borne terminally above foliage, ray florets arranged acropetally on a capitulum.

*Quantity of short days to flowering (response time).*—7.5 weeks.

*Natural season flowering.*—Not determined for this variety.

*Quantity of inflorescences per plant.*—10-14.

*Lastingness of individual blooms on the plant.*—4 weeks.

*Fragrance.*—Slightly spicy.

Bud (just when opening/showing color):

*Color.*—Closest to RHS 170D.

*Length.*—0.8 cm.

*Width.*—1.1 cm.

*Shape.*—Oblate.

Immature inflorescence:

*Diameter.*—5.3 cm.

*Color of ray florets, upper surface.*—RHS 53A with streaks of RHS 3A near the margins on the basal portion.

*Lower surface.*—Closest to RHS 3B overlain with RHS 185A.

Mature inflorescence:

*Diameter.*—9.1-9.9 cm.

*Depth.*—2.8 cm.

*Total diameter of disc.*—1.8 cm.

*Receptacle color.*—RHS 142C.

*Receptacle height.*—0.6 cm.

*Receptacle diameter.*—0.6 cm.

Ray florets:

*Average quantity of florets.*—17.

*Type.*—Ligulate.

*Color of florets, upper surface.*—Closest to RHS 53A with streaks of RHS 3A near the margins on the basal portion.

*Lower surface.*—Closest to RHS 3B overlain with RHS 185A.

*Length.*—3.7-5.3 cm.

*Width.*—1.1-1.3 cm.

*Longitudinal axis.*—Straight.

*Shape.*—Eliptical.

*Apex shape.*—Acute.

*Margin.*—Entire.

*Corolla tube.*—Short.

*Texture, upper surface.*—Papillose.

*Lower surface.*—Papillose.

Disc florets:

*Average quantity of florets.*—205.

*Color of immature florets.*—Light green.

*Color of mature florets.*—RHS 7A.

*Length.*—0.6 cm.

*Width.*—0.1 cm.

*Shape*.—Tubular, elongated.
*Apex shape*.—Acute, 5 pointed.

Phyllaries:
*Quantity*.—16-18.
*Color, upper surface*.—RHS 138A.
*Lower surface*.—RHS 138A.
*Length*.—0.9-1.6 cm.
*Width*.—0.3-0.5 cm.
*Shape*.—Lanceolate.
*Apex shape*.—Acute.
*Base*.—Fused.
*Margins*.—Entire; slightly papery.
*Texture, upper surface*.—Glabrous.
*Lower surface*.—Puberlulent.

Reproductive organs:
*Pistil*.—1, found on both types of florets.
*Length*.—0.6 cm.
*Style color*.—RHS 149D.
*Style length*.—0.5 cm.
*Stigma color*.—RHS 4B.
*Stigma shape*.—Bi-parted.
*Ovary color*.—RHS 155C but more translucent.
*Stamens*.—4, found on only on the disc florets.
*Color of filaments*.—RHS 155C.
*Length filaments*.—0.2 cm.
*Anther color*.—RHS 12A.
*Anther length*.—0.15 cm.
*Anther shape*.—Oval.
*Color of pollen*.—RHS 12A.
*Pollen amount*.—Scant.
*Fertility/seed set*.—Has not been observed to date.
*Disease/pest resistance*.—Has not been observed to date.
*Heat and cold resistance*.—Has not been determined to date.

What is claimed is:

1. A new and distinct variety of *Chrysanthemum* plant named 'CIDZ0109' substantially as illustrated and described herein.

* * * * *